United States Patent [19]

Sakamoto

[11] Patent Number: 5,334,229
[45] Date of Patent: Aug. 2, 1994

[54] ALGINATE GEL BEAD

[75] Inventor: Yuji Sakamoto, Tochigi, Japan

[73] Assignee: Kirin Beer Kabushiki Kaisha, Tokyo, Japan

[21] Appl. No.: 830,070

[22] Filed: Feb. 3, 1992

Related U.S. Application Data

[63] Continuation-in-part of Ser. No. 412,938, Sep. 26, 1989, abandoned.

[51] Int. Cl.$^5$ .............................. A01C 1/06; A01H 1/00
[52] U.S. Cl. .................................. 47/57.6; 47/58; 47/DIG. 9
[58] Field of Search ......... 47/57.612, 57.601, DIG. 9, 47/58; 435/240.45, 240.49, 240.5, 240.51

[56] References Cited

U.S. PATENT DOCUMENTS

| | | | |
|---|---|---|---|
| 2,656,649 | 10/1953 | Ostier | 47/1 |
| 3,545,129 | 12/1970 | Schreiber et al. | 47/57.6 |
| 3,688,437 | 9/1972 | Hamrin | 47/57.6 |
| 4,465,017 | 8/1984 | Simmons | 118/418 |
| 4,562,663 | 1/1986 | Redenbaugh | 47/58 |
| 4,583,320 | 4/1986 | Redenbaugh | 47/57.6 |
| 4,665,648 | 5/1987 | Branco et al. | 47/57.6 |
| 4,777,762 | 10/1988 | Redenbaugh et al. | 47/57.6 |
| 4,779,376 | 10/1988 | Redenbaugh | 47/57.6 |
| 4,803,800 | 2/1989 | Romaine et al. | 47/1.1 |
| 4,808,430 | 2/1989 | Kouno | 427/4 |

FOREIGN PATENT DOCUMENTS

| | | |
|---|---|---|
| 12968 | 1/1976 | Japan . |
| 10426 | 1/1977 | Japan . |
| 50868 | 4/1980 | Japan . |
| 65185 | 4/1982 | Japan . |
| 31991 | 2/1983 | Japan . |
| 39608 | 3/1983 | Japan . |
| 40051 | 3/1983 | Japan . |
| 205496 | 11/1983 | Japan . |
| 74984 | 4/1984 | Japan . |
| 159759 | 9/1984 | Japan . |
| 216542 | 12/1984 | Japan . |
| 118103 | 6/1985 | Japan . |
| 160885 | 8/1985 | Japan . |
| 40708 | 2/1986 | Japan . |
| 158708 | 7/1986 | Japan . |
| 262904 | 11/1987 | Japan . |

OTHER PUBLICATIONS

Suiyousei Koubunmshi et al., Technique for Most Recent Processing, Quality Improvement and Application Development of Water Soluble Polymers and Water Dispersible Polymers, pp. 147–155, May 1981, Deiei Kaihatsu Senta, Tokyo, Japan.

A Method Described in New Food Industry, vol. 28, No. 4, p. 10 (Apr. 1986) Shokuhin Shizai Kenkyukai, Tokyo.

Webster's II New Riverside University Dictionary (1984) p. 512.

Primary Examiner—David T. Fox
Assistant Examiner—Charles Rories
Attorney, Agent, or Firm—James C. Weseman

[57] ABSTRACT

Methods and materials are provided for the improved production of gel beads useful for encapsulating plant reproductive units.

17 Claims, No Drawings

ALGINATE GEL BEAD

RELATED APPLICATION DATA

This application is a continuation-in-part of commonly-owned and co-pending application Ser. No. 07/412,938, filed Sep. 26, 1989, now abandoned.

TECHNICAL FIELD

This invention relates generally to the field of agriculture and crop production and more particularly to the improved production of gel beads useful for encapsulating plant reproductive units.

BACKGROUND ART

The process of making an analog of botanic seed has been disclosed, e.g., in U.S. Pat. Nos. 4,562,663 and 4,779,376. As described therein, gel beads (or capsules) can be produced using various matrices. Among the disclosed matrix materials, alginate is considered particularly desirable because of its good gel-forming ability and economical price. However, when propagules (particularly somatic embryos, adventitious shoots, or shoot primordia) are embedded within alginate gel beads (obtained, for example, by dropping 2% sodium alginate solution containing plant propagules into 100 mM calcium chloride solution), it was observed that the propagules may emerge slowly from the bead, and some died within the bead without emergence. The reason for the poor emergence rate is believed to be the occasional low vigor of some of the propagules, which at times, was not sufficient for the propagules to emerge from the capsules. An additional limitation discovered relates to the physical characteristics of the matrix.

Alginate gel beads are also used in various commercial fields, such as in the food industry for confectionery or in the chemical industry for immobilizing carriers, because they can be prepared easily by dropping soluble alginate solutions, such as sodium alginate, into multivalent metal salt solutions, such as calcium chloride.

Certain of these uses are described in "Suiyousei Koubunshi, Mizu Bunsangata Jushi No Saishin Kako, Kaishitsugijutsu To Youto Kaihatsu Sogo Gijutsu Shiryoushuu" (Technique for Most Recent Processing, Quality Improvement and Application Development of Water Soluble Polymers and Water Dispersible Polymers), page 147-155, 1981, Keiei Kaihatsu Senta, Tokyo, Japan. In each commercial field, the merits for using alginate are indicated and some results in overcoming undesirable characteristics of alginate are reported.

For example, attempts have been made to change the undesirable texture of alginate for food applications or to stabilize and increase its low pressure-tolerance for long-term usage as immobilized carriers of chemicals. These improvements are classified into three types:
Type 1: Use of a special alginate formulation.
Type 2: Use of a substance, singly or in combination with the complexing agent, which interferes with the reaction between alginate and the complexing agent, either during the complexing process or afterwards. Alternatively, complexing agents other than the widely used calcium salt can be used.
Type 3: Addition of inactive substances (which create a discontinuous phase in the gel) to the alginate sol.

As an example of a Type 1 improvement, a method described in New Food Industry, Vol. 28, No. 4, p. 10 (1986) Shokuhin Shizai Kenkyukai, Tokyo, allows the production of a softer gel bead by using an alginate of high M/G ratio (ratio of D-mannuronic acid and L-guluronic acid).

An example of a Type 2 improvement is the use of a cation salt which does not complex sodium alginate. In Japanese Patent Application Laid-Open Publication No. 50868/1980, a softer alginate gel texture for human oral application was obtained by treating the alginate gel bead with monovalent cations after complexing with polyvalent metal ion. In Japanese Patent Application Laid-Open Publication No. 40051/1983, the gel texture for oral applications was improved by adding magnesium ion to the gel bead. In another example, Japanese Patent Application Laid-Open Publication No. 159759/1984, an improved method to make fish egg-like granules was demonstrated by adding glucono-delta-lactone into the complexing calcium solution.

To make harder immobilizing beads, an aluminum salt was used instead of calcium (Japanese Patent Application Laid-Open Publication Nos. 31991/1983 or 65185/1982). In U.S. Pat. No. 4,562,663 or Japanese Patent Application Laid-Open Publication Nos. 160885/1985, 216542/1984 or 74984/1984, methods are described in which a hard gel bead was obtained by treating the bead's surface with polymer cations, such as polyalkyleneimine, chitosan, or polyamino acid and its derivatives. Finally, in Japanese Patent Application Laid-Open Publication No. 10426/1977, zinc sulfate was used to improve alginate gel membranes for pack cosmetic material.

An example of a Type 3 improvement is disclosed in Japanese Patent Application Laid-Open Publication No. 12968/1976, in which alginate gels contain polymers which do not interact with alginate. A jelly with good texture was formed by adding natural pectin, locust bean gum and guar gum to alginate. In another example, Japanese Patent Application Laid-Open Publication No. 205496/1983, a microorganism-containing bead was formed by dropping a solution mixture containing microorganisms, sodium alginate and a polysaccharide having a carboxymethyl group into an aqueous complexing solution containing calcium ions or aluminum ions. In Japanese Patent Application Laid-Open Publication No. 39608/1983, an improved method for packing cosmetic materials by adding crystalline cellulose, filler, etc. to alginate sol was described.

For other purposes, there are examples of the use of specific complexing agents or the addition substances to the alginate sol. For example, Japanese Patent Application Laid-Open Publication No. 158708/1986, the supply of trace element was achieved by using sea water as complexing agent. In Japanese Patent Application Laid-Open Publication No. 40708/1986, an absorbent polymer was added to the alginate sol to improve water retention of the bead. In U.S. Pat. No. 3,688,437 and Japanese Patent Application Laid-Open Publication No. 262904/1987, embedded oxygen gas or air in the bead was used to supply oxygen to the seed. In Japanese Patent Application Laid-Open Publication No. 118103/1985, a method is described in which beads are complexed with biologically active substances, such as insecticides or fertilizers. In U.S. Pat. No. 4,583,320, the addition of auxiliary substances to gel beads is disclosed.

It is considered desirable to provide improved gel bead characteristics for botanic seed analog applications which include a self-breaking system in which the bead has a sufficient gel hardness for transport, handling and sowing, but becomes brittle and breaks open after sowing. To date, however, there are no known reports relating to botanic seed analogs or seed encapsulation which disclose improvements in the physical character of gel beads in regard to a self-breaking ability.

DISCLOSURE OF THE INVENTION

It is an object of this invention to provide improved methods and compositions of gel beads which facilitate emergence of enclosed propagules, particularly where the propagules have low vigor.

It is a further object of this invention to provide improved methods and compositions for self-breaking gel beads which contain plant propagules.

The present invention achieves this and other objects by providing a method for producing a gel bead containing a plant propagule which displays improved germination rate of the propagule. The present method comprises providing a complexed alginate gel bead containing at least one plant propagule. The gel bead is treated to remove excess complexing agent, then treated with at least one monovalent cation salt solution, and excess monovalent cation salt is removed to cause the bead to break open after sowing.

Also provided are gel beads produced in accordance with the present method, and complexed alginate gel beads containing plant propagules, from which excess complexing agent has been removed, and which beads nave been treated with monovalent cation salt solution and from which excess monovalent cation salt has been removed to cause the bead to break open after sowing.

DETAILED DESCRIPTION OF THE INVENTION

The present invention provides a method for producing a gel bead containing a plant propagule which displays improved germination rate of the propagule. The present method comprises providing a complexed alginate gel bead containing at least one plant propagule. The gel bead is treated to remove excess complexing agent, then treated with at least one monovalent cation salt solution, and excess monovalent cation salt is removed to cause said bead to break open after sowing.

Many methods to improve the physical character of alginate gel bead have been tried in various industrial fields, as described above. These improvements dealt with the change of texture for human oral applications or for increasing gel hardness. The present invention is directed towards improvement of propagule-containing gel beads by providing a self-breaking ability to facilitate emergence of germinating embryos.

The invention provides a desirable bead for the emergence of enclosed plant propagules by providing a complexed alginate gel bead containing a plant propagule in accordance with principles well known in the art.

To provide self-breaking beads, numerous combinations of matrix species and methods can be employed. For example, presently preferred combinations include: Complexed alginate beads which were washed thoroughly to remove excess complexing agents and immersed in a 50 mM to 2 M monovalent cation salt solution, followed by washing with water. These treatments caused the beads to swell gradually and finally break open. Alternatively, a dilute chelating solution could be used in place of water, to cause the same phenomena, but within a shorter time period.

To explain the invention in greater detail, the method can be put into practice by the following process. The complexed beads should be washed thoroughly to remove excess complexing agent. The suitable washing time is not limited, but is desirably approximately 2 to 10 hours. Then the beads are treated with sodium chloride, sodium sulfate, potassium nitrate, ammonium chloride, or ammonium sulfate as the suitable monovalent ion, but other ions are usable. By immersing the gel beads into a solution of from approximately 5 mM to 2000 mM, preferably 100 mM to 500 mM, of these salts for 5 minutes to 12 hours, the beads became brittle.

Thereafter, the beads are desalted by washing with water for approximately 10 minutes to 2 hours, preferably 15 to 45 minutes. Instead of washing, the beads can also be immersed in water for the indicated time period.

The beads obtained by the above procedures may be sown in a moistened atmosphere or soil environment so that they increase in diameter, become more brittle, and finally split. The gel beads can be stored after any of these steps in the procedure, for example, the complexing, washing, treating with monovalent cation or desalting steps.

Alternatively, a solution of a calcium chelating agent can be used to wash the beads, instead of using a moistened environment, and thereby induce the self-breaking effect. These chelating agents include sodium citrate, sodium hexametaphosphate, sodium polyphosphate and sodium ethylenediaminetetraacetate, at concentrations ranging from approximately 0.001 to 5%, preferably 0.02 to 0.5%.

By using such improved beads, the emergence rate of somatic embryos or adventitious shoots from the beads was increased 6 to 9.6 fold. The self-breaking capsules are suited for making analogs of botanic seeds, which need pressure tolerance during storage, transport and sowing, but require a certain degree of brittleness to allow emergence of propagules from beads. The self-breaking capsules retain hardness during storage but become brittle and finally break by the presence of a small amount of water applied as the beads are planted or afterwards.

The following examples serve to illustrate certain preferred embodiments and aspects of the present invention and are not to be construed as limiting the scope thereof.

EXPERIMENTAL

In the experimental disclosure which follows, all weights are given in grams (g) or milligrams (mg), all concentrations are given as millimolar (mM) or micromolar ($\mu$M) and all volumes are given in liters (L) or milliliters (mL) unless otherwise indicated.

In each of the following examples, 50 beads, each containing a lettuce adventitious shoot or celery somatic embryo as a plant propagule, were used.

EXAMPLE 1

Celery somatic embryos, obtained by the method of L. Williams and H. A. Collin (Ann. Bot. 40:325, 1976), were dispersed in 2% potassium alginate. Beads obtained by complexing with 100 mM calcium nitrate were washed for 6 hours with tap water to remove excess complexing agent. The washed beads were immersed in 500mM potassium nitrate solution for 30 minutes followed by washing with water for 20 minutes. After this treatment, the beads swelled and became brittle.

These beads were sowed on vermiculite at 20° C. and 7000 lux. After three weeks, all beads had split and 4% had produced shoots and roots.

COMPARISON 1

Beads containing celery somatic embryos were produced as described in Example 1, with the exception of the potassium nitrate and water treatments. Beads had not split and only 4% of the beads produced shoots and roots.

EXAMPLE 2

Lettuce adventitious shoots (3 mm in length), produced in accordance with the method of Kadkade (Nature 270:50, 1977), were encapsulated as described in Example 1, instead of celery somatic embryos. All beads had split and 96% of the beads produced shoots and roots.

COMPARISON 2

Lettuce adventitious shoots, produced as described in Example 1, were dispersed in 2% sodium alginate solution. Beads containing lettuce adventitious shoots were produced as described in Example 1, with the exception of the potassium nitrate and water treatments.

Only 10% of the beads produced shoots and roots on vermiculite after 14 days at 20° C. and 12,000 lux, as compared to 96% for Example 2.

It should be understood that various alternatives to the methods and materials herein disclosed may De employed in practicing the present invention. It is intended that the following claims define the invention, and that the materials and methods within the scope of these claims and their equivalents be covered thereby.

I claim:

1. A method for producing a gel bead for encapsulating a plant propagule, which bead possesses the capability of self-breaking, the method comprising the steps of:
    (a) providing a gel bead comprising complexed alginate;
    (b) removing excess complexing agent from said gel bead;
    (c) treating said gel bead with a solution containing at least one monovalent cation salt selected from the group consisting of sodium salts, potassium salts, and ammonium salts; and
    (d) removing excess monovalent cation salt from said gel bead thereby causing said bead to break open after sowing.

2. The method of claim 1 wherein said gel bead comprises at least one plant propagule.

3. The method of claim 2 wherein said monovalent cation salt is at least one selected from the group consisting of potassium salts.

4. The method of claim 2 wherein the excess complexing agent is removed by washing said bead for approximately two to about ten hours.

5. The method of claim 2 wherein the concentration of monovalent cation salt solution is approximately 5 mM to about 2000 mM.

6. The method of claim 2 wherein said bead is treated with the monovalent cation salt solution for a time ranging from approximately five minutes to about 12 hours.

7. The method of claim 2 wherein the excess monovalent cation salt is removed by washing said bead for approximately 10 minutes to about two hours.

8. The method of claim 2 wherein said plant propagule is at least one selected from the group consisting of somatic embryos, adventitious shoots, and shoot primordia.

9. The method of claim 2 wherein said plant propagule displays an improved germination rate.

10. A gel bead produced by the method of claim 1.

11. The method of claim 10 wherein the gel bead comprises at least one plant propagule.

12. The gel bead of claim 11 wherein the monovalent cation salt is at least one selected from the group consisting of potassium salts.

13. The gel bead of claim 11 wherein the excess complexing agent is removed by washing said bead for approximately two to about 10 hours.

14. The gel bead of claim 11 wherein the concentration of monovalent cation salt solution is approximately 5 mM to about 2000 mM.

15. The gel bead of claim 11 wherein the bead is treated with the monovalent cation salt solution for a time ranging from approximately five minutes to about twelve hours.

16. The gel bead of claim 11 wherein the excess monovalent cation salt is removed by washing said bead for approximately 10 minutes to about two hours.

17. The gel bead of claim 11 wherein said plant propagule is at least one member selected from the group consisting of somatic embryos, adventitious shoots, and shoot primordia.

* * * * *